(12) United States Patent
Huth et al.

(10) Patent No.: US 7,923,469 B2
(45) Date of Patent: Apr. 12, 2011

(54) COMPOSITIONS INCLUDING VITAMIN-BASED SURFACTANTS AND METHODS FOR USING SAME

(75) Inventors: Stanley Huth, Newport Beach, CA (US); Richard Chadwick, Orange, CA (US); Gerry Franco, Trabuco Canyon, CA (US)

(73) Assignee: Allergen, Inc., Irvine, CA (US)

( * ) Notice: Subject to any disclaimer, the term of this patent is extended or adjusted under 35 U.S.C. 154(b) by 1045 days.

(21) Appl. No.: 10/131,848

(22) Filed: Apr. 24, 2002

(65) Prior Publication Data
US 2003/0068250 A1    Apr. 10, 2003

Related U.S. Application Data

(60) Provisional application No. 60/287,430, filed on Apr. 30, 2001.

(51) Int. Cl.
*A61K 31/355*    (2006.01)
(52) U.S. Cl. ........................................ 514/458; 514/912
(58) Field of Classification Search .................. 514/458, 514/912
See application file for complete search history.

(56) References Cited

U.S. PATENT DOCUMENTS

| | | | |
|---|---|---|---|
| 3,278,447 A | 10/1966 | McNicholas | |
| 3,910,296 A | 10/1975 | Karageozian et al. | |
| 4,367,157 A | 1/1983 | Sherman | |
| RE32,672 E | 5/1988 | Huth et al. | |
| 4,758,595 A | 7/1988 | Ogunbiyi et al. | |
| 4,820,352 A | 4/1989 | Riedhammer et al. | |
| 4,836,986 A | 6/1989 | Ogunbiyi et al. | |
| 5,179,122 A | 1/1993 | Greene et al. | |
| 5,235,073 A | 8/1993 | Kim et al. | |
| 5,422,073 A | 6/1995 | Mowrey-McKee et al. | |
| 5,593,637 A | 1/1997 | Mowrey-McKee et al. | |
| 5,603,929 A | 2/1997 | Desai et al. | |
| 5,653,695 A | 8/1997 | Hopkins et al. | |
| 5,653,972 A | 8/1997 | Desai et al. | |
| 5,719,110 A | 2/1998 | Cook | |
| 5,736,165 A | 4/1998 | Ripley et al. | |
| 5,817,277 A | 10/1998 | Mowrey-McKee et al. | |
| 5,886,030 A | 3/1999 | Maniar | |
| 6,046,143 A | 4/2000 | Khan et al. | |
| 6,136,850 A * | 10/2000 | Park et al. ................ | 514/458 |

FOREIGN PATENT DOCUMENTS

| | | |
|---|---|---|
| EP | 0358447 | 3/1990 |
| EP | 0734732 | 10/1996 |
| EP | 0848055 | 6/1998 |
| ES | 2166306 | 4/2002 |
| WO | 93/04706 | 3/1993 |
| WO | 96/14829 | 5/1996 |
| WO | 99/26607 | 6/1999 |
| WO | 00/35499 | 6/2000 |
| WO | 00/35500 | 6/2000 |
| WO | 00/35861 | 6/2000 |
| WO | 00/59475 | 10/2000 |

* cited by examiner

*Primary Examiner* — Zohreh A Fay
(74) *Attorney, Agent, or Firm* — Kevin Forrestal

(57) ABSTRACT

Compositions for caring for contact lenses and eyes include a liquid aqueous medium and a vitamin derivative component present in an amount effective as a surfactant in the composition. The compositions can be used to clean, soak, re-wet and, with the inclusion of a disinfectant, disinfect contact lenses. In addition, the compositions are effective as artificial tears and eye wash solutions. Methods for contact lens care and eye care are also disclosed.

1 Claim, No Drawings

COMPOSITIONS INCLUDING VITAMIN-BASED SURFACTANTS AND METHODS FOR USING SAME

RELATED APPLICATION

This application claims benefit of Provisional Application Ser. No. 60/287,430 filed Apr. 30, 2001.

BACKGROUND OF THE INVENTION

The present invention relates to compositions and methods for contact lens care and eye care. More particularly, the invention relates to compositions which include Vitamin derivatives useful as surfactants in such compositions and to methods of contact lens care and eye care using such compositions.

Nonionic surfactants are preferred for use in the contact lens care and eye care applications due to their relatively lower adverse interaction with contact lens polymers and ocular tissues than cationic, amphoteric and anionic surfactants. Nonionic surfactants are also preferred from the perspective of minimizing adverse interaction with cationic disinfecting agents, such as polyhexamethylene biguanide (PHMB) and the like, commonly employed in contact lens multi-purpose solutions.

Current surfactants used in contact lens multi-purpose solutions, re-wetting and in-the-eye cleaning solutions are exemplified by the surfactants disclosed in U.S. Pat. No. 4,836,986. This patent discloses that when used, the preferred neutral or non-ionic surfactants impart cleaning and conditioning properties and are usually present in amounts up to about 15 weight percent. The surfactant should be soluble in the lens care solution, non-irritating to eye tissues and usually have a hydrophilic-lipophile balance (HLB) of about 12.4 to about 18.8. Satisfactory non-ionic surfactants include, without limitation, polyethylene glycol esters of fatty acids, e.g. coconut, polysorbate, polyoxyethylene or polyoxypropylene ethers of high alkanes ($C_{12}$-$C_{18}$).

One group of non-ionic surfactants, poly(oxypropylene)-poly(oxyethylene) adducts of ethylene diamine having a molecular weight about 7,500 to about 27,000 wherein at least about 40 weight percent of the adducts is poly(oxyethylene), have been found to be particularly advantageous for use in cleaning and conditioning both soft and hard contact lenses when used in amounts from about 0.01 to about 15 weight percent. The CTFA Cosmetic Ingredient Dictionary's adopted name for this group of surfactants is poloxamines. Such surfactants are available from BASF Wyandotte Corp., Wyandotte, Mich., under the registered trademark "Tetronic". An analogous series of surfactants is the poloxamer series, which are polyoxyethylene, polyoxypropylene block polymers available from BASF Wyandotte Corp., Parsippany, N.J. 07054 under the trademark "Pluronic".

U.S. Pat. No. 4,820,352 discloses the use of poloxamine surfactants in general as cleaning agents in combination with biguanide disinfectants. U.S. Pat. Nos. 5,817,277, 5,593,637 and 5,422,073 disclose a contact lens multi-purpose solution comprising a polyhexamethylene biguanide (PHMB) disinfectant in combination with the surfactants tyloxapol, poloxamine, or poloxamer for cleaning and disinfecting contact lenses.

One concern with current contact lens care, in-the-eye rewetting, artificial tear solutions and eye wash compositions, and the surfactants therein, pertains to a lack of beneficial effects on ocular tissues. That is to say, existing surfactants perform, e.g. clean, well, but do not provide additional benefits to the ocular tissues with which they come in contact.

Another concern with current surfactants pertains to systemic absorption. A significant amount of any solution, which is placed into the eye, is washed out, for example, through the naso-lacrimal ducts into the gastrointestinal tract, where systemic absorption can occur. Current surfactants, despite being compatible with lens care solutions and comfortable to the eye, are not known to be metabolically degraded or useful.

A number of patents disclose Vitamin E derivatives, some of which are surfactants. U.S. Pat. No. 5,179,122 discloses a nutritional supplement containing Vitamin E, a Vitamin E surfactant and an inert carrier. U.S. Pat. No. 5,235,073 discloses polyethoxylated Vitamin E with surfactant activity.

Several patents disclose Vitamin E or its derivatives in combination with preservatives of the same type utilized in contact lens care and ophthalmic applications. U.S. Pat. Nos. 5,653,695 and 6,046,143 disclose a medical device having a surface with a water soluble lubricant thereon and a water-soluble lubricant, the lubricant consisting of a silicone surfactant, Vitamin E or its derivatives and polyhexamethylenebiguanide to inhibit microbial growth. Vitamin E and its derivatives are disclosed as being oily products, which enhance the lubricity of the lubrication system. Water-soluble derivatives of Vitamin E, including Vitamin E surfactants, are not disclosed.

U.S. Pat. Nos. 5,603,929 and 5,653,972 disclose preserved, storage-stable ophthalmic compositions comprising acidic drugs, a polymeric quaternary ammonium compound and boric acid, and methods for controlling ocular inflammation using such compositions. Vitamin E tocopheryl polyethylene glycol 1000 succinate is disclosed as a formulation component. U.S. Pat. No. 5,886,030 discloses the use of Vitamin E tocopheryl derivatives, including Vitamin E tocopheryl polyethylene glycol 1000 succinate, in anti-inflammatory ophthalmic compositions. Methods are disclosed for treating or controlling ocular inflammation and for improving comfort and reducing irritation in compositions containing ophthalmic therapeutic agents, which are irritating to the eye. The compositions may include preservatives such as benzalkonium chloride, Polyquad™ and Dymed™ (polyhexamethylenebiguanide).

It would be advantageous to provide contact lens care compositions and compositions for use in the eye, and methods for using such compositions, including surfactants which provide one or more additional benefits, for example, to ocular tissues and/or systemically to the human or animal in whose eye the composition is placed.

SUMMARY OF THE INVENTION

New ophthalmic compositions, for example, for use in disinfecting and/or cleaning and/or otherwise treating contact lenses, and/or for in the eye use, and methods for using such compositions have been discovered. In general, the present invention involves vitamin-based surfactants included in such compositions, for example, multi-purpose contact lens care compositions, preferably solutions, useful for disinfecting, cleaning, rinsing, re-wetting, storing and otherwise treating contact lenses. In addition, such vitamin-based surfactants, can be included in in-the-eye solutions or compositions useful for re-wetting contact lenses in the eye and in other compositions useful for in-the-eye applications, such as artificial tear compositions, eye wash compositions, irrigating compositions and the like. Such compositions have been found to be very effective in use with the vitamin-based surfactants being very effective as surfactants in such compositions. Importantly, the vitamin-based surfactants have been found to provide additional benefits, for example, vitamin-related benefits to the individual, for example human or animal, in whose eye a contact lens treated with the present composition is worn or in whose eye the present composition is placed. The present compositions are straightforward, ophthalmically acceptable, relatively easy to manufacture and use.

In one embodiment, compositions effective for disinfecting a contact lens are provided. Such compositions comprise a liquid aqueous medium; a disinfectant component present in the composition in an amount effective to disinfect contact lenses contacted with the composition and a vitamin derivative component present in an amount effective as a surfactant in the composition.

The vitamin derivative components preferably are soluble in the liquid aqueous medium of the present compositions. Although derivatives of any vitamin may be employed in accordance with the present invention, provided that such vitamin derivative is effective as a surfactant in the present compositions, particularly useful vitamin derivative components include one or more derivatives of a vitamin selected from Vitamin A, Vitamin A2, Vitamin C, Vitamin D1, Vitamin D2, Vitamin D3, Vitamin D4, Vitamin E, Vitamin K1, vitamin K2 and mixtures thereof. A particularly useful vitamin derivative component includes at least one derivative of vitamin E. In a very useful embodiment, the present vitamin derivative component includes Vitamin E tocopheryl polyethylene glycol succinate, for example, Vitamin E tocopheryl polyethylene glycol 1000 succinate, hereinafter Vitamin E TPGS.

In another very useful embodiment, the present vitamin derivative component includes Vitamin E tocopheryl polyethylene glycol succinamide, for example, Vitamin E tocopheryl polyethylene 1000 succinamide, hereinafter Vitamin E TPGSA, wherein the ester bond between polyethylene glycol and succinic acid in Vitamin E TPGS is replaced with an amide bond.

In one embodiment, the present compositions are in the form of multi-purpose contact lens care solutions.

Although any suitable contact lens disinfectant component may be employed in accordance with the present invention, the disinfectant component preferably is a non-oxidative disinfectant. In one useful embodiment, the disinfectant component comprises one or more biguanides. A very useful disinfectant component comprises polyhexamethylene biguanide.

The present compositions, in one embodiment, are useful for cleaning contact lenses. In such embodiments, the vitamin derivative component preferably is present in an amount effective to at least assist in removing, more preferably in an amount effective to remove, deposit material from a contact lens contacted with the composition.

In another broad aspect in the present invention, compositions effective for in-the-eye use are provided and comprise a liquid aqueous medium; and a vitamin derivative component present in the amount effective as a surfactant in the composition. Such compositions are ophthalmically acceptable and adapted for use in one or more in-the-eye applications. Preferably, such compositions are adapted for use as one or more of contact lens re-wetters, in-the-eye cleaners, artificial tear compositions, eye wash compositions, irrigating compositions for use in the eye, for example, compositions useful as irrigants during surgery, and the like.

Preferably, the present compositions are substantially free of steroidal anti-inflammatory agents, nonsteroidal anti-inflammatory agents, sulfa drugs and poorly soluble ophthalmic agents. The present compositions may be substantially free of any pharmaceutically active component effective to provide a therapeutic effect.

In one useful embodiment, the present compositions useful for in-the-eye applications include an effective amount of a preservative component, many of which are conventional and well known in the art. Although any suitable preservative component may be employed in the present compositions, a very useful preservative component comprises a chlorite, such as stabilized chlorine dioxide. Stabilized chlorine dioxide is very effective as a preservative in the present compositions. In addition, stabilized chlorine dioxide has few if any harmful side effects to either the composition or the eye in which the composition is placed.

Methods for disinfecting contact lenses are also provided. Such methods comprise contacting a contact lens with the present disinfectant component containing compositions at conditions effective to disinfect the contact lens.

In addition, methods for treating contact lenses are provided and comprise contacting a contact lens with a composition in accordance with the present invention at conditions effective to provide the desired treatment of or to the contact lens. For example, methods for cleaning contact lenses are provided and comprise contacting a deposit material-containing contact lens with a composition in accordance with the present invention at conditions effective to remove deposit material, for example, proteinaceous deposit material, from the deposit material-containing contact lens.

Methods for treating an eye are provided and comprise administrating an effective amount of the present compositions to the eye.

Each and every feature described herein, and each and every combination of two or more of such features, is included within the scope of the present invention provided that the features included in such a combination are not mutually inconsistent.

DETAILED DESCRIPTION

The present invention can be used in solutions intended for use with all contact lenses such as soft, rigid and soft or flexible gas permeable, silicone hydrogel, silicone non-hydrogel and conventional hard contact lenses. The present invention can be used in ocular solutions not intended for contact lenses, such as artificial tear, eyewash compositions, irrigating compositions and the like.

In one embodiment, the present compositions are useful as multi-purpose compositions for contact lens care. A multi-purpose composition, as used herein, is useful for cleaning, rinsing, disinfecting, rewetting, storing or otherwise treating a contact lens, while out of the eye. Such multi-purpose compositions are also useful for re-wetting and cleaning contact lenses, while the lenses are in the eye. Products useful for re-wetting and cleaning contact lenses while the lenses are in the eye are often termed re-wetters or "in-the-eye" cleaners. The present compositions are also useful as re-wetters or "in-the-eye" cleaners. The term "cleaning" as used herein includes the loosening and/or removal of deposits and other contaminants from a contact lens with or without digital manipulation and with or without an accessory device that agitates the solution. The term "re-wetting" as used herein refers to the addition of water over at least a part, for example, at least a substantial part, of at least the anterior surface of a contact lens.

The present compositions are useful as artificial tear compositions, which are used to relieve dry eye and other symptoms of ocular discomfort. The present compositions are useful as eyewash and irrigating compositions, for example, solutions and eye lotions, which can be used to wash, bath, flush or rinse the eye following exposure to a foreign entity, such as a chemical material or a foreign body. Foreign entities in this context include, without limitation, one or more of pollen, dust, ragweed and other foreign antigens, which cause allergic reactions such as redness, itching and burning, and the like. The use of simple saline eye drops has been shown to be effective in 30-35% of cases of seasonal allergic conjunctivitis. The vitamin derivative components of the present amidated with succinic acid and polyalkylene glycol, e.g., polyethylene glycol 1000. Folic acid can be esterified or amidated at either of its two free carboxylic acid groups by polyalkylene glycol, e.g., polyethylene glycol 1000. Non-anionic Vitamin E derivatives are particularly preferred.

Two very useful Vitamin E derivative-based surfactants are D-alpha-tocopheryl polyethylene glycol 1000 succinate (Vitamin E TPGS), and its amide analogue (Vitamin E TPGSA). The structure of Vitamin E TPGS is represented as follows:

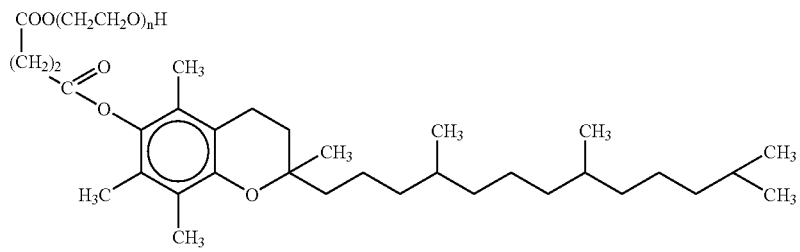

compositions advantageously exceed the effects of simple saline in relieving or treating or managing the symptoms of seasonal allergic conjunctivitis.

The vitamin derivative components useful in the compositions and methods of the present invention provide very effective wetting and/or cleaning of contact lenses both in and out of the eye and in-eye wetting and/or cleaning of exposed ocular tissues. The vitamin derivative components of the present invention are substantially non-toxic and/or non-irritating and/or non-damaging to the eye, can provide a cell and tissue protective function for ocular cells and tissues, and can provide metabolically useful sources of vitamins upon ocular and systemic absorption.

As used herein, a vitamin derivative component or vitamin-based surfactant component includes a vitamin derivatized with a chemical structure such that the resulting moiety is effective as a surfactant in the present compositions and/or methods. Without wishing to limit the invention to any particular theory of operation, it is believed that the vitamin derivative components of the present invention form micelles and have a critical micelle concentration. Such components can at least assist in cleaning contact lenses in or out of the eye, can at least assist in removing, preferably can remove foreign particulates, debris, antigens and the like from the eye and are ophthalmically acceptable and/or substantially non-toxic to the eye.

Vitamin-based surfactants in accordance with the present invention can be used alone or in combination or mixtures with one another. Vitamins A, A2, C, D1, D2, D3, D4, E, K1, K2 and folic acid are preferred vitamins which can be derivatized to form surfactants in accordance with the present invention. Any suitable vitamin derivative can be employed provided such derivative is effective to function as described herein, for example, as a surfactant. Examples of such derivatives include, but not limited to, the succinic acid ester or amide of Vitamin A (retinol), which can be prepared and then further esterified or amidated (e.g., coupled with an amide bond) with a polyalkylene glycol, for example, selected from polyethylene glycols, polypropylene glycols, mixtures thereof and the like, to form a suitable surfactant. Polyethylene glycol 1000 is one very useful polyalkylene glycol. Vitamins D1, D2, D3 or D4 can be similarly esterified or amidated to form suitable surfactants. The dihydro derivatives of Vitamins K1 and K2 can be prepared and thereafter esterified or Vitamin E TPGS is a polyethylene glycol (PEG) ester of D-alpha-tocopheryl acid succinate, where the polyethylene glycol (PEG) molecular weight is about 1000. D-alpha-tocopheryl acid succinate is, in turn, a succinic acid ester of D-alpha-tocopherol, Vitamin E. Vitamin E TPGSA is a polyethylene glycol (PEG) amide of D-alpha-tocopheryl acid succinate, containing an amide bond between the PEG chain and the distal succinic acid free acid group, and where the PEG molecular weight is about 1000. The structure of TPGSA is represented as follows.

Vitamin E TPGS is highly soluble in water and is an excellent source of biologically active Vitamin E when given systemically. It has an amphiphilic nature, where the PEG part of the molecule is hydrophilic and the Vitamin E succinate structure is hydrophobic. Given this amphiphilic nature, Vitamin E TPGS is a surface-active agent (surfactant) and is believed to form micelles and/or various liquid crystalline phases in water as well as foam. Vitamin E TPGS is a member of the polyethylene glycol class of nonionic surfactants. It has a hydrophilic/lipophilic (HLB) balance of about 13.2. Vitamin E TPGS is an excellent emulsifier and cleaning agent. The critical micelle concentration (CMC), the concentration of a surfactant above which micelles form, in water is about 0.02 w/v % at 37° C. for Vitamin E TPGS.

The surfactant concentration employed preferably exceeds the critical micelle concentration of the particular surfactant component used.

The vitamin derivative component is present in the compositions of the present invention in an amount effective to act as a surfactant in the present compositions. Such amount can vary widely based on the actual vitamin derivative or derivatives being used, the application for which the composition is being provided, the chemical make-up of the composition and the like factors. Such vitamins derivative components advantageously are employed in an amount of at least about 0.01%, more preferably about 0.01% to about 0.5% or about 1.0%, and still more preferably about 0.02% to about 0.20%, by weight of the composition.

Other Vitamin E-based surfactant components can also be used in the present invention. All of the naturally occurring Vitamin E compounds that exhibit at least part of the biological activity of α-tocopherol and their corresponding synthetic forms can be used to form surfactants for use in the present invention. Vitamin E compounds useful for the present invention include, without limitation, α-, β-, χ-, and δ-tocopherol and α-, β-, χ-, and δ-tocotrienol. All these compounds occur as a variety of isomers. The commercially available synthetic forms of Vitamin E comprise an approximately equal mixture of eight sterioisomeric forms of α-tocopherol. The presently useful surfactants can be based on a single vitamin isomer or a mixture of vitamin isomers.

A variety of surfactant forms of vitamins such as Vitamin E or other vitamins, can be produced and are useful in the present invention. These surfactants can be produced with known synthetic chemistry methodology, for example, direct esterification or amidation of the phenolic OH group of tocopherol with a surfactant chain such as polyethylene glycol or a second esterification or amidation of a primary-ester intermediate such as Vitamin E succinate. Esterification of the phenolic OH group of tocopherol is a preferred chemical synthetic path. The vitamin-based esters are preferred for use as surfactants in accordance with the present invention. Ester or amide bonds are readily hydrolyzed by enzymes, such as enzymes, with esterase or amidose activity in-vivo, which leads directly to the production of biologically active vitamins. Ocular tissues are known to contain esterases and amidoses which hydrolyze ester and amide bonds, respectively in ocular prodrugs. Thus, ocular tissue esterases or amidoses can act upon the ester or amide bonds in, for example, Vitamin E TPGS and other ester-based vitamin surfactants to release biologically active vitamins to tissues.

Vitamin-based surfactants which have ester structures are often sufficiently stable to substantially and effectively maintain surfactant activity in the aqueous compositions, e.g., solutions, of the present invention. Other types of surfactants can be produced with other in-vivo labile bonds which also lead to the production of biologically active vitamins, provided that such surfactants have sufficient stability in aqueous solution to provide an acceptable level of surfactant activity. Amide bonds, as an example, are estimated to be several orders of magnitude more hydrolytically stable than ester bonds. Nonionic surfactants are preferred. Under certain conditions, for example, where the activity of the disinfecting agent is not compromised and in-eye safety and comfort can be maintained, cationic, amphoteric and anionic surfactants can also be employed. A variety of nonionic surfactant classes may be produced based on a vitamin precursor and used in the present invention, such as the polyethylene glycol surfactants. Other nonionic surfactant classes corresponding to the presently useful vitamin-based surfactant components include, without limitation, the polyoxyethylated linear alcohols, nonoxynols, octoxynols, polyoxyethylated dodecylamines, sorbitan monoesters and the like and mixtures thereof.

The surfactants useful in the present invention advantageously are water-soluble when used alone or as a mixture. Such surfactants preferably have HLB values of about 12 to about 13 when used alone. In addition, the surfactant or surfactants employed preferably produce a clear solution in accordance with the present invention.

Vitamin E TPGS is known to be unstable with respect to hydrolysis upon exposure to acidic and alkaline pH conditions. The instability is due to acid- or base-catalyzed hydrolysis of the ester linkages. As pH approaches neutrality in buffered solutions, Vitamin E TPGS becomes more stable. This can be problematic for some compositions, as pH 7.5 is more optimal for ocular comfort, since it is closer to the human tear pH of 7.45. Therefore, compositions of the present invention can also optionally include the hydrolysis products of Vitamin E surfactant ester bond hydrolysis, to further stabilize the surfactant ester against hydrolysis during shelf storage. The mechanism of stabilization is believed to be based upon known chemical equilibrium and kinetic theory and more particularly, a principle known as Le Chatelier's Principle. Thus, compounds such as succinic acid and polyethylene glycol 1000 can each be employed alone or in combination to stabilize Vitamin E TPGS in aqueous solution, as such compounds are hydrolysis products of ester bond hydrolysis of Vitamin E TPGS. Hydrolysis products of ester forms of other vitamin-based surfactants can also be used in a similar manner to stabilize the surfactant as well as provide an additional source of vitamin.

Hydrolysis of Vitamin E TPGS to Vitamin E tocopherol hemisuccinate and polyethylene glycol can result in a solution which is incompatible with disinfecting agents such as polyhexamethylene biguanide (PHMB). This is because it has been found that in some cases the amount of Vitamin E tocopherol hemisuccinate anion which forms can substantially ion-pair the cationic PHMB, thus reducing or neutralizing PHMB antimicrobial activity. Hydrolysis of Vitamin E TPGS in aqueous solution is quite slow and in most cases results in part-per-million concentrations of hydrolysis products. Nonetheless, this may be sufficient to inactivate a disinfecting agent such as PHMB or other cationic antimicrobial agents. In such cases, an alternative amide-based surfactant, such as Vitamin E TPGSA, may be advantageously employed. It may be useful to suppress hydrolysis of the Vitamin E TPGS. Such suppression may be achieved by using Le Chatelier's Principle, employing small amounts of polyethylene glycol, for example, PEG 1000, and succinic acid, buffering the solution at a slightly acidic pH of about 6.8-6.9, and using a sterically-hindered, non-complexing buffer, such as Bistris, 2-(bis(2-hydroxyethyl)amino)-2(hydroxy-methyl)-1,3-propanediol. The relatively bulky hydrophilic hydroxyethyl groups of Bistris act to shield the basic nitrogen and make it more difficult for this buffer to serve as a base-catalyst for ester hydrolysis. It is preferred to use more stable amide-based vitamin surfactant in compositions containing conventional amounts of PHMB (for example, about 0.5 ppm to about 1 ppm) where such compositions may otherwise result in unstable Vitamin E TPGS.

The vitamin-based surfactants of the present invention can also be used together with conventional non-vitamin surfactants, for example, nonionic, cationic, anionic and amphoteric non-vitamin surfactants. The vitamin-based surfactants, if used in combination with one or more non-vitamin surfactants are preferably used with nonionic non-vitamin surfactants.

A liquid aqueous medium or other material is "rophthalmically acceptable" when it is compatible with ocular tissue, that is, it does not cause significant or undue detrimental effects when brought into contact with ocular tissue. Preferably, the ophthalmically acceptable material is also compatible with other components of the present compositions.

The present compositions may, and preferably do, further comprise a disinfectant component. The amount of the disinfectant component present in the liquid aqueous medium is effective to disinfect a contact lens placed in contact with the composition.

When a disinfectant component is desired to be included in an instant composition, it may be oxidative or non-oxidative.

Particularly useful oxidative disinfectant components are hydrogen peroxide and/or one or more other peroxy-containing compounds, for example, one or more other peroxides.

For hydrogen peroxide, a 0.5% (w/v) concentration, for example, in an aqueous liquid medium is often effective as a disinfectant component. It is preferred to use at least about 1.0% or about 2.0% (w/v) hydrogen peroxide which concentrations reduce the disinfecting time over that of the 0.5% (w/v) peroxide concentration. No upper limit is placed on the amount of hydrogen peroxide which can be used in this invention except as limited in that the disinfectant component should have no substantial detrimental effect on the contact lens being treated or on the eye of the wearer of the treated contact lens. An aqueous solution containing about 3% (w/v) hydrogen peroxide is very useful.

So far as other peroxides are concerned, they should be used in effective disinfecting concentrations.

When an oxidative disinfectant is used in the present invention, a reducing or neutralizing component in an amount sufficient to chemically reduce or neutralize substantially all of the oxidative disinfectant, for example, hydrogen peroxide, present is employed.

Such reducing or neutralizing components are preferably incorporated into the enzyme component-containing tablet. The reducing agent is generally any non-toxic reducing agent. Reducing components include SH (group)-containing water-soluble lower alcohols, organic amines and salts thereof, amino acids and di- or tripeptides, e.g., cysteine hydrochloride ethyl ester, gluthione, homocysteine, carbamoyl cysteine, cysteinylglycine, 2-mercaptopropionic acid, 2-mercaptopropionylglycine, 2-mercaptoethylamine hydrochloride, cysteine, n-acetylcysteine, beta mercaptoethanol, cysteine hydrochloride, dithiothreitol, dithioerythritol, sodium bisulfate, sodium metabisulfite, thio urea, sulfites, pyrosulfites and dithionites such as the alkali metal salts or alkaline earth metal salts of sulfurous acid, pyrosulfurous acid and dithionious acid, e.g., lithium, sodium, calcium and magnesium salts and mixtures thereof. The thiols are preferred, with N-acetylcysteine being particularly useful.

In general, the reducing component is used in amounts in the range of about 0.5% to about 10% (w/v) of the liquid medium.

In one embodiment, all or a portion of the reducing component is replaced by a catalase component which acts to catalyze the neutralization or decomposition of the oxidative disinfectant component, such as hydrogen peroxide. Such catalase component can be included, for example, in the core of a barrier component coated tablet, in an amount effective to, together with the reducing component, if any, destroy or cause the destruction of all the oxidative disinfectant component present in the liquid medium. Some catalase component may be advantageously used to increase the rate at which the oxidative disinfectant component is destroyed.

The disinfectant component is preferably a substantially non-oxidative disinfectant component. As used herein, non-oxidative disinfectant components include effectively non-oxidative organic chemicals which derive their antimicrobial activity through a chemical or physiochemical interaction with the microbes or microorganisms. Suitable non-oxidative disinfectant components are those generally employed in ophthalmic applications and include, but are not limited to, quaternary ammonium salts used in ophthalmic applications such as poly[dimethylimino-2-butene-1,4-diyl]chloride, alpha-[4-tris(2-hydroxyethyl) ammonium]-dichloride (chemical registry number 75345-27-6, available under the trademark Polyquaternium 1® from Onyx Corporation), benzalkonium halides, and biguanides such as salts of alexidine, alexidine-free base, salts of chlorhexidine, hexamethylene biguanides and their polymers, antimicrobial polypeptides, and the like and mixtures thereof. A particularly useful substantially non-oxidative disinfectant component is selected from one or more (mixtures) of tromethamine (2-amino-2-hydroxymethyl-1,3 propanediol), polyhexamethylene biguanide (PHMB), N-alkyl-2-pyrrolidone, chlorhexidine, Polyquaternium-1, hexetidine, bronopol, alexidine, very low concentrations of peroxide, ophthalmically acceptable salts thereof, and the like.

The salts of alexidine and chlorhexidine can be either organic or inorganic and are typically disinfecting gluconates, nitrates, acetates, phosphates, sulphates, halides and the like. Generally, the hexamethylene biguanide polymers, also referred to as polyaminopropyl biguanide (PAPB) or polyhexamethylene biguanide (PHMB), have molecular weights of up to about 100,000. Such compounds are known and are disclosed in U.S. Pat. No. 4,758,595.

The non-oxidative disinfectant components useful in the present invention are preferably present in the liquid aqueous medium in concentrations in the range of about 0.00001% to about 2% (w/v).

More preferably, the non-oxidative disinfectant component is present in the liquid aqueous medium at an ophthalmically acceptable or safe concentration such that the user can remove the disinfected lens from the liquid aqueous medium and thereafter directly place the lens in the eye for safe and comfortable wear.

When a contact lens is desired to be disinfected by a disinfectant component, an amount of disinfectant effective to disinfect the lens is used. Preferably, such an effective amount of the disinfectant reduces the microbial burden on the contact lens by one log order, in three hours. More preferably, an effective amount of the disinfectant reduces the microbial load by one log order in one hour.

The disinfectant component in accordance with the present invention is preferably provided in the liquid aqueous medium, and is more preferably soluble in the liquid aqueous medium.

The present compositions may further comprise effective amounts of one or more additional components, such as an additional cleaning component, for example, an enzyme component and the like; a conditioning component; a wetting component; a wearability component, a buffer component, a tonicity adjustor component; and the like and mixtures thereof. The additional component or components may be selected from materials which are known to be useful in contact lens care compositions and are included in amounts effective to provide the desired effect or benefit. When an additional component is included, it is preferably compatible under typical use and storage conditions with the other components of the composition. For instance, when a disinfectant component is provided, the aforesaid additional component or components are preferably substantially stable in the presence of the disinfectant.

Each of the additional components, if any, may be present in either the solid or liquid form of the present compositions. When the additional component or components are present as a solid, they can either be intimately admixed such as in a powder or compressed tablet or they can be substantially separated, although in the same particles, as in an encapsulated pellet or tablet. When the combination of vitamin-based surfactant component and additional component or components is in liquid form, they are typically soluble in the liquid aqueous medium. One or both of the vitamin-based surfactant component and the additional component or components can be in solid form until desired to be used, whereupon they can be dissolved in the liquid aqueous medium in order to effectively contact the surface of a contact lens.

When an additional cleaning component is included in the present compositions, the cleaning component should be present in an amount effective to at least facilitate removing, and preferably effective to remove, debris or deposit material from a contact lens. Exemplary cleaning components include detergents or surfactants such as nonionic surfactants, for example, polysorbates (such as polysorbate 20-Trademark Tween 20), 4-(1,1,3,3-tetramethylbutyl) phenol polymers (such as the polymer sold under the trademark Tyloxapol), ethylene oxide/propylene oxide block copolymers, glycolic esters of fatty acids and the like, anionic surfactants, for example, alkyl ether sulfates and the like, and mixtures thereof.

The amount of surfactant component, if any, present varies over a wide range depending on a number of factors, for example, the specific vitamin-based surfactant component being used, the specific non-vitamin surfactant or surfactants, if any, being used, the other components in the composition and the like. Often the total amount of surfactant component is in the range of about 0.005% to about 0.1% or about 0.5% (w/v) of the liquid medium.

Cleaning enzymes may also be employed. A cleaning enzyme component can be provided in an amount effective to at least facilitate removing deposit material from the contact lens. Types of deposit material or debris which may be deposited on the lens include proteins, lipids, and carbohydrate-based or mucin-based debris. One or more types of debris may be present on a given lens.

The cleaning enzyme component employed may be selected from enzymes conventionally employed in the enzymatic cleaning of contact lenses. Among the preferred enzymes are proteases, lipases, and the like. Exemplary enzymes are described by Huth et al U.S. Pat. No. 32,672 RE and Karageozian et al U.S. Pat. No. 3,910,296, which disclosures are incorporated herein by reference.

Preferred proteolytic enzymes are those substantially free of sulfhydryl groups or disulfide bonds, the presence of which may react with active oxygen of the oxidative disinfectant, rendering the enzyme inactive. Metalloproteases, enzymes which contain a divalent metal ion, may also be used.

Yet a more preferred group of proteolytic enzymes are the serine proteases, such as those derived from *Bacillus* and *Streptomyces* bacteria and *Aspergillus* molds. Of this class of enzymes, still more preferred enzymes are those derived from alkaline proteases, generically referred to as subtilisin enzymes.

Other enzymes preferred for this application include pancreatin, trypsin, collaginase, keratinase, carboxylase, aminopeptidase, elastase, and aspergillopeptidase A and B, pronase E (from *S. griseus*) and dispase (from *Bacillus polymyxa*).

In one embodiment, a liquid aqueous medium containing such a cleaning enzyme component preferably has sufficient enzyme to provide about 0.001 to about 3 Anson units of activity, more preferably about 0.01 to about 1 Anson units, per single lens treatment. However, higher or lower amounts may be used. Moreover, since enzyme activity is pH dependent, the preferred pH range for an enzyme can be determined by the skilled practitioner.

A particularly noteworthy embodiment of the present compositions is substantially free of proteolytic enzyme. Such a formulation provides for effective contact lens cleaning without the need to rinse the lens after cleaning to free the lens of the enzyme.

Compositions of the invention can also include preservatives, stabilizers, color indicators of hydrogen peroxide decomposition, plasticizers, thickening agents and the like.

Acceptable effective concentrations for these additional components in the compositions of the invention are readily apparent to the skilled practitioner.

The present compositions may include an effective amount of a preservative component. Any suitable preservative or combination of preservatives may be employed. Examples of suitable preservatives include, without limitations, benzalkonium chloride, methyl and ethyl parabens, hexetidine, phenyl mercuric salts and the like and mixtures thereof. The amounts of preservative components included in the present compositions are such to be effective in preserving the compositions and can vary based on the specific preservative component employed, the specific composition involved and the like factors. Preservative concentrations often are in the range of about 0.00001% to about 0.05% or about 0.1% (w/v) of the composition.

Very useful examples of preservative components in the present invention include, but are not limited to, chlorite components. Specific examples of chlorite components useful as preservatives in accordance with the present invention include stabilized chlorine dioxide (SCD), metal chlorites such as alkali metal and alkaline earth metal chlorites, and the like and mixtures thereof. Technical grade (or USP grade) sodium chlorite is a very useful preservative component. The exact chemical composition of many chlorite components, for example, SCD, is not completely understood. The manufacture or production of certain chlorite components is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purite® by Bio-Cide International, Inc.

The liquid aqueous medium used is selected to have no substantial deleterious effect on the lens being treated, or on the wearer of the treated lens or on the human or animal in whose eye the present composition is placed. The liquid medium is constituted to permit, and even facilitate, the instant lens treatment or treatments or in-the-eye applications. The liquid aqueous medium advantageously has a pH in the range of about 5 or about 6 to about 8 or about 10, and an osmolality in the range of at least about 150 mOsmol/kg, for example, about 300 or about 350 to about 400 mOsmol/kg. The liquid aqueous medium more preferably is substantially isotonic or hypotonic (for example, slightly hypotonic) and/or is ophthalmically acceptable. The liquid aqueous medium preferably includes an effective amount of a tonicity adjusting component to provide the liquid medium with the desired tonicity. The liquid aqueous medium of the present invention preferably includes a buffer component which is present in an amount effective to maintain the pH of the medium in the desired range. Such tonicity adjusting components and buffer components may be present in the liquid aqueous medium and/or may be introduced into the liquid aqueous medium.

Particularly useful media are those derived from saline, e.g., a conventional saline solution, or buffered saline solution. In addition, the liquid aqueous media may include one or more other materials, for example, as described elsewhere herein, in amounts effective to treat the contact lens and/or ocular tissues (for example, provide a beneficial property to the contact lens and/or ocular tissues) contacted with such media.

The compositions of the present invention may include viscosity modifying agents such as cellulose polymers, including hydroxypropyl methyl cellulose (HPMC), hydroxyethyl cellulose (HEC), ethyl hydroxyethyl cellulose, hydroxypropyl cellulose, methyl cellulose and carboxymethyl cellulose; carbomers (e.g. Carbopol®); polyvinyl alcohol; polyvinyl pyrrolidone; alginates; carrageenans; and guar, karaya, agarose, locust bean, tragacanth and xanthan gums. The concentration of such viscosity modifiers will vary between about 0.01 to about 5% w/v.

The compositions of the present invention may include a buffer. A variety of conventional buffers may be employed, such as phosphate, borate, citrate, acetate, histidine, tris, bis-tris and the like. Borate buffers include boric acid and its salts, such as sodium or potassium borate. Potassium tetraborate or potassium metaborate, which produce boric acid or its salt in solution, may also be employed. Hydrated salts such as sodium borate decahydrate can also be used. Phosphate buffers include phosphoric acid and its salts, for example, $M_2HPO_4$ and $MH_2PO_4$, wherein M is an alkali metal salt such as Na and K. Hydrated salts can also be used, such as $Na_2HPO_4.7H_2O$ and $NaH_2PO_2.H_2O$. The term phosphate also includes compounds that produce phosphoric acid or its salt in solution. Additionally, organic counter-ions for the above buffers may also be employed. The concentration of buffer generally varies from about 0.05 to about 2.5 w/v % and more preferably varies from about 0.05 to about 0.5 w/v %. The type and amount of buffer are selected so that the formulation meets the functional performance criteria of the solution, such as surfactant stability, antimicrobial efficacy and buffer capacity. The buffer is also selected to provide a pH, which is compatible with the eye and any contact lenses with which it is intended for use. Generally, a pH close to that of human tears, pH 7.45, is very useful, although a wider pH range from about 5.0 to about 8.5, more preferably about 6.0 to about 8.0 and most preferably about 6.8 to about 7.8 is also acceptable. In one embodiment, the present composition has a pH of about 7.0.

It is desirable in some instances to include sequestering agents in the present solutions in order to bind metal ions, which might otherwise stabilize cell membranes of microorganisms and thus interfere with optimal disinfection activity. Alternatively, it is desirable in some instances to bind metal ions to prevent their interaction with other species in solution. Sequestering agents are usually added in amounts ranging from about 0.01 to about 0.2 w/v %. Examples include Ethylene-diaminetetraacetic acid (EDTA) and its potassium or sodium salts and low molecular weight organic acids such as citric and tartaric acids and their salts, e.g., sodium salts.

Typically, the aqueous solutions of the present invention are adjusted with tonicity agents, to approximate the osmotic pressure of normal tear fluid, which is equivalent to a 0.9 w/v % solution of sodium chloride. Examples of suitable tonicity adjusting agents include, but are not limited to: sodium, potassium, calcium and magnesium chloride, dextrose, glycerin and propylene glycol. These agents are typically used individually in amounts ranging from about 0.001 to about 2.5 w/v %. Preferably, the solutions will contain about 0.14 w/v % potassium chloride and about 0.006 w/v % each of calcium and magnesium chloride, the latter two compounds in the absence of sequestering agents, if possible. These amounts have been found to be optimal for maintaining ocular tissue integrity. Preferably, the tonicity agent(s) will be employed in an amount to provide a final osmotic value of about 150 to about 450 mOsm/kg, more preferably between about 250 to about 350 mOsm/kg and most preferably between about 270 to about 320 mOsm/kg.

Methods for treating a contact lens using the herein described compositions are included within the scope of the invention. Such methods comprise contacting a contact lens with such a composition at conditions effective to provide the desired treatment to the contact lens.

The contacting temperature is preferred to be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time in the range of about 5 minutes or about 1 hour to about 12 hours or more.

The contact lens can be contacted with the liquid aqueous medium by immersing the lens in the medium. During at least a portion of the contacting, the liquid medium containing the contact lens can be agitated, for example, by shaking the container containing the liquid aqueous medium and contact lens, to at least facilitate removal of deposit material from the lens. After such contacting step, the contact lens may be manually rubbed to remove further deposit material from the lens. The cleaning method can also include rinsing the lens substantially free of the liquid aqueous medium prior to returning the lens to a wearer's eye.

In addition, methods of applying or administering artificial tears, washing eyes and irrigating ocular tissue, for example, before, during and/or after surgical procedures, are included within the scope of the present invention. The present compositions, having suitable chemical make-ups, are useful in each of these, and other, in-the-eye applications. These compositions can be used in in-the-eye applications in conventional and well known manners. In other words, a composition in accordance with the present invention can be used in an in-the-eye application in a substantially similar way as a conventional composition is used in the identical application. One or more of the benefits of the present compositions, as discussed elsewhere herein, are provided as the result of such in-the-eye use.

The following non-limiting examples illustrate certain aspects of the present invention.

The amount of the surfactant or other components or ingredients in solution according to the present invention refers to the amount formulated and introduced into the solution at the time the solution is made.

EXAMPLE 1

Contact Lens Multi-Purpose Solution with Vitamin E TPGS

A concentration of 0.06 w/v % Vitamin E TPGS is selected to incorporate into a contact lens multi-purpose solution as the only surfactant cleaner, as this concentration exceeds the CMC concentration and thus meets the FDA requirement for surfactants in multi-purpose solutions. The multi-purpose solution formulation is represented in Table 1.

TABLE 1

| Ingredient | % w/v Conc. |
|---|---|
| Hydroxypropylmethylcellulose | 0.15 |
| Disodium Edetate | 0.02 |
| Sodium Chloride | 0.79 |
| Potassium Chloride | 0.14 |
| Vitamin E TPGS | 0.06 |
| Polyhexamethylene biguanide | 0.00011 |

TABLE 1-continued

| Ingredient | % w/v Conc. |
|---|---|
| Sodium Phosphate Dibasic 7H$_2$O | 0.12 |
| Sodium Phosphate Monobasic H$_2$O | 0.01 |
| Purified Water | qs ad 100 |

Polyhexamethylene biguanide (PHMB) is the disinfecting agent in this formulation. The formulation in Table 1 is substantially similar to a control disinfection formulation without Vitamin E TPGS and which contains a nonionic surfactant, Poloxamer 237 at 0.05 w/v %. This control formula is currently marketed by Allergan, Inc. as Complete® Comfort Plus™ Multi-Purpose Solution.

The solution set forth in Table 1 is prepared by first adding the hydroxypropylmethylcellulose (HPMC) to about 65% of the purified water in a glass vessel and heating this to 50° C. while vigorously stirring. Vitamin E TPGS (Eastman Chemical Company, Kingsport, Tenn.) is added to this solution after about 20 minutes when the solution has been allowed to cool to 45° C. The heat is turned off and the solution is allowed to cool while stirring overnight. The remaining components, except the PHMB, are added to about 35% of the purified water at room temperature, allowing each to dissolve before adding the next. This solution is added to the solution containing the HPMC and the Vitamin E TPGS. A small amount of purified water is used for rinsing and quantitatively transferring the solution. The pH of the mixed solution is determined to be 7.18, which does not require adjustment. The appropriate amount of a PHMB stock solution at 0.0503 w/v % is added to a final PHMB concentration of 0.00011 w/v %. The final solution is sterile filtered through a 0.22 micron cellulose acetate filtration membrane for antimicrobial activity testing.

Antimicrobial activity of the formulation set forth in Table 1 and the aforementioned control solution is assessed using an industry-standard method for measuring disinfection efficacy of a contact lens multi-purpose solution. This method involves challenging the solution with an inoculum of approximately $10^5$ to $10^6$ colony forming units (CFU)/ml of each of five microorganisms representing the FDA Contact Lens Disinfection Panel. Various periods of contact time with the solution are allowed, followed by neutralizing the remaining disinfectant and culturing remaining viable organisms. The remaining viable organisms are represented as recovery in cfu/ml at a particular contact time. Lastly, the reduction in viable organisms is calculated for each contact time as a base-10 log drop from the initial inoculum.

The two solutions were initially challenged with approximately $10^5$ to $10^6$ CFU/ml level of S. aureus and C. albicans as the initial screening panel and assayed at 2 and 4 hours. A minimum of a 4 hour soak is currently approved and recommended for disinfection and protein removal for Complete® Comfort Plus™ Multi-Purpose Solution. The results are presented in Table 2.

TABLE 2

| | Composition 1 | | Control | |
|---|---|---|---|---|
| Organism & Contact Time | Recovery cfu/ml | Log drop | Recovery cfu/ml | Log drop |
| S. aureus ATCC 6538 6.3 × 10e5 inoculum | | | | |
| 2 hour | $5.5 \times 10^3$ | 2.1 | $1.2 \times 10^3$ | 2.7 |
| 4 hour | $7.0 \times 10^2$ | 3.0 | $3.3 \times 10^2$ | 3.3 |
| C. albicans ATCC 10231 6.0 × 10e5 inoculum | | | | |
| 2 hour | $2.0 \times 10^5$ | 0.5 | $2.2 \times 10^5$ | 0.4 |
| 4 hour | $2.7 \times 10^5$ | 0.4 | $1.6 \times 10^5$ | 0.6 |

The results show that the antimicrobial activity of the two solutions is essentially identical, given that test variation is often several tenths of a log drop at any given test time. Given these favorable results, antimicrobial efficacy is repeated using the full antimicrobial panel of test organisms. The results are presented in Table 3.

TABLE 3

| | Composition 1 | | Control | |
|---|---|---|---|---|
| Organism and Contact Time | Recovery cfu/ml | Log drop | Recovery cfu/ml | Log drop |
| S. marcescens ATCC 13880 3.5 × $10^5$ inoculum | | | | |
| 2 hour | <10 | 5.5 | <10 | 5.5 |
| 4 hour | <10 | | <10 | |
| 6 hour | <10 | | <10 | |
| S. aureus ATCC 6538 4.9 × $10^5$ inoculum | | | | |
| 2 hour | $2.0 \times 10^3$ | | $4.0 \times 10^2$ | |
| 4 hour | $3 \times 10^1$ | 4.2 | <10 | 5.7 |
| 6 hour | <10 | | <10 | |
| P. aeruginosa ATCC 9027 3.1 × $10^5$ inoculum | | | | |
| 2 hour | <10 | 5.5 | <10 | 5.5 |
| 4 hour | <10 | | <10 | |
| 6 hour | <10 | | <10 | |
| C. albicans ATCC 10231 3.5 × $10^5$ inoculum | | | | |
| 4 hour | $2.4 \times 10^5$ | 0.1 | $1.7 \times 10^5$ | 0.3 |
| 6 hour | $1.5 \times 10^5$ | | $1.1 \times 10^5$ | |
| 24 hour | $2.1 \times 10^4$ | | $9.7 \times 10^4$ | |
| F. solani ATCC 36031 1.5 × $10^5$ | | | | |
| 2 hour | $1.0 \times 10^4$ | | $2.6 \times 10^4$ | |
| 4 hour | $3.5 \times 10^3$ | 1.7 | $3.4 \times 10^3$ | 1.7 |
| 6 hour | $1.0 \times 10^3$ | | $4.0 \times 10^4$ | |

TABLE 4

| | Average log reduction at 4 hours | |
|---|---|---|
| Organism and Number of Tests | Composition 1 | Control |
| S. marcescens ATCC 13880 (n = 1) | 5.5 | 5.5 |

TABLE 4-continued

| Organism and Number of Tests | Average log reduction at 4 hours | |
|---|---|---|
| | Composition 1 | Control |
| S. aureus ATCC 6538 (n = 2) | 3.6 | 4.5 |
| P. aeruginosa ATCC 9027 (n = 1) | 5.5 | 5.5 |
| C. albicans ATCC 10231 (n = 1) | 0.3 | 0.5 |
| F. solani ATCC 36031 (n = 1) | 1.7 | 1.7 |

These results confirm the first antimicrobial efficacy test. Table 4 presents a summary of the two antimicrobial efficacy tests at the 4 hour contact time. The results show a 0.9 log reduction in activity for Composition 1 vs the control solution for S. aureus, which in this case is not considered significant, as any log reduction of S. aureus exceeding 3.0 is considered acceptable.

EXAMPLE 2

Contact Lens Multi-Purpose Solutions with Vitamin E TPGS

A series of 4 contact lens multi-purpose solutions containing 3 concentrations of Vitamin E TPGS at 2 different pH values are prepared to evaluate antimicrobial disinfection efficacy, cytotoxicity and stability. A fifth solution is prepared without Vitamin E TPGS to serve as a control. This solution contains a standard nonionic surfactant, Pluronic F87, also known as Poloxamer 237.

The solutions are prepared as follows: 3 liters of a stock solution of 0.90 w/v % HPMC, F4M grade is prepared. Approximately 2 liters of purified water is heated to 70° C. while vigorously stirring. 27.0 grams of HPMC is added and the solution is stirred and heated at between 60-70° C. for about 2-3 hours. The heat is turned off, the solution is adjusted to a final volume of 3 liters and stirring is continued until the solution is used. A 1.0 w/v % stock solution of Vitamin E TPGS is prepared by adding 10.0 grams of Vitamin E TPGS (Eastman Chemical Company, Kingsport, Tenn.) to about 900 ml of purified water at 45° C. while stirring vigorously. The solution is stirred for 4 hours with heating at 40-45° C. until the Vitamin E TPGS is completely dissolved. The heat is turned off and the solution is allowed to stand overnight. Purified water is added to the Vitamin E TPGS solution to adjust the total volume to 1 liter. 4-liter glass flasks are used to make 3 liters of each of the final solution formulas listed in Table 5. The individual salts are weighed, added and dissolved in approximately 2 liters of purified water in each flask in the order listed in Table 5 before adding the next salt. Pluronic F87 was weighed and added to solution Formula 1 prior to adding the glycerine. Thereafter, 500 ml of the HPMC stock solution is added to formula 1. 3.198 ml of a 0.1032 w/v % stock solution of PHMB is then added to the Formula 1 solution. Lastly, the solution is adjusted to a final volume of 3.000 liters with purified water.

The Vitamin E TPGS solutions are made in a similar manner, with the exception that the Vitamin E TPGS is added after the HPMC. 180 ml of the Vitamin E TPGS stock solution is added to each of formulas 2 and 3. 90 and 300 ml of the Vitamin E TPGS stock solution, respectively, are added to formulas 4 and 5. 3.198 ml of the PHMB stock solution are added to each of formulas 2-5 and the solutions is adjusted to a final volume of 3.000 liters.

All solutions are sterile filtered through a 0.22 micron cellulose acetate filtration membrane for further testing. Solution Formulas 1-3 are filled into 4 oz. high density polyethylene plastic bottles for stability evaluation. Solution Formulas 4 and 5 are stored in clear plastic containers or glass. Table 5 summarizes the formulations and initial physical and chemical assay results.

TABLE 5

| Excipient (w/v%) | Formula 1 control | Formula 2 | Formula 3 | Formula 4 | Formula 5 |
|---|---|---|---|---|---|
| Na2HPO4.-7H2O | 0.12 | 0.12 | 0.08 | 0.08 | 0.08 |
| NaH2PO4.-H2O | 0.01 | 0.01 | 0.028 | 0.028 | 0.028 |
| NaCl | 0.69 | 0.69 | 0.69 | 0.69 | 0.69 |
| KCl | 0.14 | 0.14 | 0.14 | 0.14 | 0.14 |
| Glycerine | 0.2 | 0.2 | 0.2 | 0.2 | 0.2 |
| HPMC | 0.15 | 0.15 | 0.15 | 0.15 | 0.15 |
| Vitamin.E-TPGS | | 0.06 | 0.06 | 0.03 | 0.1 |
| Pluronic F87 | 0.05 | | | | |
| PHMB | 0.00011 | 0.00011 | 0.00011 | 0.00011 | 0.00011 |
| pH, adj if necess.* | 7.5 | 7.5 | 7 | 7 | 7 |
| Purified Water | qs ad 100 | qs ad 100 | qs ad 100 | qs ad 100 | qs ad 100 |
| PHMB t(o) meas. | 1.12 ppm | 1.09 ppm | 0.81 ppm | 0.97 ppm | 0.97 ppm |
| pH t(o) meas. | 7.52 | 7.53 | 6.95 | 6.94 | 6.95 |
| Osm t(o) mosm/kg | 293 | 289 | 284 | 281 | 282 |
| Surface tension t(o)** | 41.2 | 40.8 | 41.6 | 41.4 | 40.3 |

*adjust pH with 1N NaOH or 1N HCl;
**dyne/cm

Three concentrations of Vitamin E TPGS were evaluated: 0.03, 0.06 and 0.10 w/v %. Two solution pH values were evaluated, one at pH 7.5 and the other at pH 7.0. pH 7.5 preferred for ocular comfort, as it is closer to the human tear pH of 7.45. pH 7.0 is advantageous for aqueous stability of Vitamin E TPGS. Contact lens disinfection efficacy of the formulations in Table 5 tested approximately 1 week after manufacture is summarized in Tables 6 and 7. F. solani is not tested as all of these formulations are expected to achieve acceptable activity against this organism.

TABLE 6

| Organism and Contact Time | Formula 1 Recovery cfu/ml | Formula 2 Recovery cfu/ml | Formula 3 Recovery cfu/ml | Formula 4 Recovery cfu/ml | Formula 5 Recovery cfu/ml |
|---|---|---|---|---|---|
| S. marcescens ATCC 13880 4.6 × 10e5 inoculum | | | | | |
| 2 hour | $1.0 \times 10^2$ | $2.7 \times 10^2$ | $2.9 \times 10^2$ | $9.0 \times 10^1$ | $1.0 \times 10^2$ |
| 4 hour | <10 | $4.5 \times 10^2$ | $1.0 \times 10^2$ | $1.0 \times 10^1$ | <10 |
| 6 hour | <10 | <10 | <10 | <10 | <10 |

TABLE 6-continued

| Organism and Contact Time | Formula 1 Recovery cfu/ml | Formula 2 Recovery cfu/ml | Formula 3 Recovery cfu/ml | Formula 4 Recovery cfu/ml | Formula 5 Recovery cfu/ml |
|---|---|---|---|---|---|
| *S. aureus* ATCC 6538 $6.5 \times 10e5$ inoculum | | | | | |
| 2 hour | $2.3 \times 10^3$ | $2.2 \times 10^3$ | $1.2 \times 10^3$ | $1.3 \times 10^3$ | $6.4 \times 10^2$ |
| 4 hour | $1.6 \times 10^2$ | $4.0 \times 10^1$ | $6.0 \times 10^1$ | $2.6 \times 10^2$ | $1.7 \times 10^2$ |
| 6 hour | $5.0 \times 10^1$ | <10 | $3.0 \times 10^1$ | $2.0 \times 10^1$ | $9.0 \times 10^1$ |
| *P. aeruginosa* ATCC 9027 $3.0 \times 10e5$ inoculum | | | | | |
| 2 hour | <10 | <10 | <10 | $4.0 \times 10^1$ | <10 |
| 4 hour | <10 | <10 | <10 | <10 | <10 |
| 6 hour | <10 | <10 | <10 | <10 | <10 |
| *C. albicans* ATCC 10231 $2.8 \times 10e5$ inoculum | | | | | |
| 2 hour | $5.7 \times 10^4$ | $7.8 \times 10^4$ | $6.0 \times 10^4$ | $6.2 \times 10^4$ | $6.0 \times 10^4$ |
| 4 hour | $4.0 \times 10^4$ | $5.0 \times 10^4$ | $5.0 \times 10^4$ | $3.7 \times 10^4$ | $4.0 \times 10^4$ |
| 6 hour | $2.7 \times 10^4$ | $1.5 \times 10^4$ | $2.0 \times 10^4$ | $2.5 \times 10^4$ | $2.5 \times 10^4$ |

TABLE 7

| | Organism & Contact Time | | | | | |
|---|---|---|---|---|---|---|
| Result | SA* 4 hr log drop | SA 4 hr D-value** | SA 6 hr log drop | CA*** 4 hr log drop | CA 6 hr log drop | CA 6 hr D-value |
| Formula 1 Control | 3.61 | 66.5 | 4.11 | 0.85 | 1.02 | 352.9 |
| Formula 2 .06% TPGS | 4.21 | 57.0 | 5.81 | 0.75 | 1.27 | 283.5 |
| Formula 3 .06% TPGS | 4.03 | 60.0 | 4.34 | 0.75 | 1.15 | 313.0 |
| Formula 4 .03% TPGS | 3.40 | 70.6 | 4.51 | 0.88 | 1.05 | 342.9 |
| Formula 5 0.1% TPGS | 3.58 | 67.0 | 3.86 | 0.85 | 1.05 | 342.9 |

*SA = *S. aureus*;
**Decimal reduction value = time in minutes to reduce challenge by 1 log;
***CA = *C. albicans*

The results in Tables 6 and 7 show that the antimicrobial activity of Formulas 2-5 containing Vitamin E TPGS is equal to that of the control solution, Formula 1. All solutions possess more than adequate disinfection activity.

Cytotoxicity of the formulations in Table 5 is evaluated with several standard cytotoxicity assays. These include the neutral red retention assay to evaluate cellular membrane damage and the Alamar Blue assay to evaluate inhibition of metabolic activity. The results of these assays indicate that all of the solutions are non-cytotoxic. These results are consistent with contact lens multi-purpose solutions which are generally comfortable for contact lens wearers.

The chemical stability of formulations 1-3 in Table 5 are evaluated over a 1 month period with physical and chemical assays for osmolality, pH, PHMB, Vitamin E TPGS degradation and surface tension. Vitamin E TPGS degradation is monitored with an HPLC assay which quantified Vitamin E TPGS. Stability samples are stored at 25, 40, 50, 60 and 70° C.

Osmolality remains substantially constant at all temperatures with the exception of 70° C., where at 4 weeks time, Formulas 1, 2 and 3 had slight increases to 301, 297 and 295 mOsm/kg. This increase is only 8, 8 and 11 mOsm/kg for the three solutions, respectively. These increases are believed to be due to water loss via transpiration through the bottles at this high temperature.

Solution pH remains within 0.1 pH units of the original values, with the exception of samples stored at 60° and 70° C. Formulas 1, 2 and 3 had pH values of 7.42, 7.31 and 6.85 at 60° C. and pH values of 7.17, 7.18 and 6.74 at 70° C., respectively, after 4 weeks storage. The drop in pH is consistent with the hydrolytic degradation of the Pluronic F87 in Formula 1 and Vitamin E TPGS in Formulas 2 and 3 at these temperatures.

PHMB concentration remains essentially unchanged at 25, 40 and 50° C. after 4 weeks storage. The concentration of PHMB in Formulas 1, 2 and 3 dropped to 0.56, 0.58 and 0.77 ppm at 60° C. and 0.36, 0.22 and 0.33 ppm at 70° C., respectively, after 4 weeks storage. These losses are not unexpected for such high temperature stresses for these formulations. The data indicate that antimicrobial activity will be maintained over a reasonable shelf life, since the shelf life specification for PHMB in some current contact lens multi-purpose solutions is 0.6-1.2 ppm and the degradation rate acceleration factor vs room temperature can easily be >18 at 60° C.

Vitamin E TPGS is more stable in Formula 3 than in Formula 2, as expected, since Formula 3 is at pH 7.0 and Formula 2 is at pH 7.5 at time zero. Vitamin E TPGS reaches a concentration of 0.0344% in Formula 2 and 0.0479% in Formula 3 after 4 weeks at 70° C. No change in Vitamin E TPGS concentration was observed at 25° or 40° C. in either Formula 2 or 3. Some changes in concentration were observed at 50° and 60° C. in both formulas. An Arrhenius analysis of Vitamin E TPGS degradation was completed using the data from 50, 60 and 70° C. for Formula 2. The small projected loss of Vitamin E TPGS is surprising and confirms the functional capability of Vitamin E TPGS in such a solution.

Changes in surface tension are observed, again principally at the higher temperatures. The amount of a particular vitamin-based surfactant to use in a composition should take into account how much of the surfactant is lost during the product shelf life. The amount of surfactant should be such as to remain above the critical micelle concentration (CMC) during the shelf life of the product.

EXAMPLE 4

Artificial Tear and Eyewash Solution

An artificial tear and eyewash solution in accordance with the present invention is prepared by blending together the various ingredients. This solution has a composition as set forth in Table 8.

TABLE 8

| Ingredient | % w/v Conc. |
| --- | --- |
| Sodium Carboxymethylcellulose | 0.50 |
| Sodium Chloride | 0.39 |
| Boric Acid | 0.60 |
| Sodium Borate Decahydrate | 0.035 |
| Potassium Chloride | 0.14 |
| Calcium Chloride (Dihydrate) | 0.006 |
| Magnesium Chloride (Hexahydrate) | 0.006 |
| Vitamin E TPGS | 0.06 |
| Purite* | 0.0050 |
| Sodium Hydroxide 1N | pH 7.2 |
| Hydrochloric Acid 1N | pH 7.2 |
| Purified Water | qs ad 100 |

*Purite is a trademark for stabilized chlorine dioxide
This solution is tested and found to be effective to provide artificial tears to a human and as an eye wash for a human.

EXAMPLE 5

Contact Lens Multi-Purpose Solution with Vitamin A Polyethyleneglycol 1000 Succinate (Vitamin A RPGS)

Vitamin A polyethyleneglycol 1000 succinate, Vitamin A RPGS, is prepared via conventional synthetic chemistry methodology by esterifying Retinol with succinic acid at the free alcohol group of Retinol and thereafter esterifying the remaining free carboxylic acid group of succinic acid with polyethyleneglycol 1000.

This Vitamin A RPGS is used in producing a multi-purpose contact lens care solution by blending together the various ingredients. The composition of this solution is shown in Table 9.

TABLE 9

| Ingredient | % w/v Conc. |
| --- | --- |
| Hydroxypropylmethylcellulose | 0.15 |
| Disodium Edetate | 0.02 |
| Sodium Chloride | 0.79 |
| Potassium Chloride | 0.14 |
| Vitamin A RPGS | 0.10 |
| Polyhexamethylene biguanide | 0.00011 |

TABLE 9-continued

| Ingredient | % w/v Conc. |
| --- | --- |
| Sodium Phosphate Dibasic 7H$_2$O | 0.12 |
| Sodium Phosphate Monobasic H$_2$O | 0.01 |
| Purified Water | qs ad 100 |

This solution is tested and is found to be effective in caring for contact lenses.

EXAMPLE 6

Artificial Tear and Eyewash Solution

An artificial tear and eyewash solution in accordance with the present invention is prepared by blending together the various ingredients. This solution has a composition as set forth in Table 10.

TABLE 10

| Ingredient | % w/v Conc. |
| --- | --- |
| Sodium Carboxymethylcellulose | 0.50 |
| Sodium Chloride | 0.39 |
| Boric Acid | 0.60 |
| Sodium Borate Decahydrate | 0.035 |
| Potassium Chloride | 0.14 |
| Calcium Chloride (Dihydrate) | 0.006 |
| Magnesium Chloride (Hexahydrate) | 0.006 |
| Vitamin A RPGS | 0.10 |
| Purite | 0.0050 |
| Sodium Hydroxide 1N | pH 7.2 |
| Hydrochloric Acid 1N | pH 7.2 |
| Purified Water | qs ad 100 |

This solution is tested and found to be effective to provide artificial tears to a human and as an eye wash for a human.

EXAMPLE 7

Artificial Tear and Eyewash Solution with Folic Acid Polyethyleneglycol 1000

Folic acid polyethylene glycol is prepared via conventional synthetic chemistry methodology by esterifying one or both of the free acid groups with polyethylene glycol 1000.

This folic acid polyethyleneglycol is used in producing an artificial tear and eye wash solution in accordance with the present invention by blending together the various ingredients. This solution has a composition as set forth in Table 11.

TABLE 11

| Ingredient | % w/v Conc. |
| --- | --- |
| Sodium Carboxymethylcellulose | 0.50 |
| Sodium Chloride | 0.39 |
| Boric Acid | 0.60 |
| Sodium Borate Decahydrate | 0.035 |
| Potassium Chloride | 0.14 |
| Calcium Chloride (Dihydrate) | 0.006 |
| Magnesium Chloride (Hexahydrate) | 0.006 |

TABLE 11-continued

| Ingredient | % w/v Conc. |
| --- | --- |
| Folic Acid | 0.10 |
| Polyethyleneglycol 1000 | |
| Purite | 0.0050 |
| Sodium Hydroxide 1N | pH 7.2 |
| Hydrochloric Acid 1N | pH 7.2 |
| Purified Water | qs ad 100 |

This solution is tested and found to be effective to provide artificial tears to a human and as an eye wash for a human.

EXHIBIT 8

Another Contact Lens Multi-Purpose Solution with Vitamin E TPGS

A concentration of 0.05 w/v % Vitamin E TPGSA (amide) is selected to incorporate into a contact lens multi-purpose solution as the only surfactant cleaner, as this concentration exceeds the CMC concentration and thus meets the FDA requirement for surfactants in multi-purpose solutions. The multi-purpose solution formulation is represented in Table 12.

TABLE 12

| Ingredient | % w/v Conc. |
| --- | --- |
| Hydroxypropylmethylcellulose | 0.15 |
| Taurine | 0.05 |
| Disodium Edetate | 0.01 |
| Sodium Chloride | 0.71 |
| Potassium Chloride | 0.14 |
| Vitamin E TPGSA (amide) | 0.05 |
| Polyhexamethylene biguanide | 0.00014 |
| Bis-tris | 0.73 |
| PEG 1000 | 0.10 |
| Purified Water | qs ad 100 |
| pH | 6.8 |

The antimicrobial efficacy of this composition is equal to or greater than the antimicrobial efficacy of the solution of Example 1.

While this invention has been described with respect to various specific examples and embodiments, it is to be understood that the invention is not limited thereto and that it can be variously practiced within the scope of the following claims.

What is claimed is:

1. A method of disinfecting a contact lens comprising contacting a contact lens with a composition at conditions effective to disinfect said contact lens, the composition comprising:

a liquid aqueous medium;

a disinfectant component present in said composition in an amount effective to disinfect a contact lens contacted with said composition; and a water soluble Vitamin E derivative component present in an amount in a range of about 0.01% to about 1.0% by weight effective as a surfactant in said composition, wherein the Vitamin E derivative component is Vitamin E TPGSA.

* * * * *